(12) United States Patent
Rivat et al.

(10) Patent No.: US 11,654,398 B2
(45) Date of Patent: May 23, 2023

(54) FILTRATION ASSEMBLY AND METHOD FOR MICROBIOLOGICAL TESTING

(71) Applicant: Merck Patent GmbH, Darmstadt (DE)

(72) Inventors: Philippe Rivat, Dorlisheim (FR); Mathieu Arrault, Dabo (FR); Vincent Schaal, Geispolsheim (FR)

(73) Assignee: Merck Patent GmbH, Darmstadt (DE)

(*) Notice: Subject to any disclaimer, the term of this patent is extended or adjusted under 35 U.S.C. 154(b) by 427 days.

(21) Appl. No.: 16/644,587

(22) PCT Filed: Sep. 4, 2018

(86) PCT No.: PCT/EP2018/073674
§ 371 (c)(1),
(2) Date: Mar. 5, 2020

(87) PCT Pub. No.: WO2019/048402
PCT Pub. Date: Mar. 14, 2019

(65) Prior Publication Data
US 2021/0060494 A1 Mar. 4, 2021

(30) Foreign Application Priority Data
Sep. 6, 2017 (EP) .................................... 17290113

(51) Int. Cl.
*B01D 61/18* (2006.01)
*B01D 63/08* (2006.01)
(Continued)

(52) U.S. Cl.
CPC ........... *B01D 63/087* (2013.01); *B01D 61/18* (2013.01); *B01D 63/081* (2013.01); *B01L 3/502* (2013.01);
(Continued)

(58) Field of Classification Search
None
See application file for complete search history.

(56) References Cited

U.S. PATENT DOCUMENTS 5,603,900 A * 2/1997 Clark .................... B29C 66/727
422/550
6,358,730 B1 * 3/2002 Kane ...................... C12M 23/10
435/297.5

(Continued)

FOREIGN PATENT DOCUMENTS

| CN | 101024813 A | 8/2007 |
| EP | 1826263 A1 | 8/2007 |

(Continued)

OTHER PUBLICATIONS

Office Action dated Dec. 3, 2021 in corresponding Chinese Examination 201880057633.2 (pp. 1-9).

(Continued)

*Primary Examiner* — Neil N Turk
(74) *Attorney, Agent, or Firm* — Millen White Zelano & Branigan, PC; Brion P. Heaney

(57) ABSTRACT

The invention concerns a filtration assembly (1) for microbiological testing and a method of using the filtration assembly for that purpose. The filtration assembly (1) comprises a ring-like membrane support (10) holding a filtration membrane (11), a cylindrical reservoir (20) of which opposite axial ends have openings and one axial opening is removably and fluid-tightly attachable to the membrane support (10) to define a sample volume adjacent to the filtration membrane (11) on one axial side of the membrane support (10); and a drain member (30) removably and fluid tightly attachable to the membrane support (10) to define a drain channel space adjacent to the filtration membrane (11) on an opposite axial side of the membrane support (10).

19 Claims, 12 Drawing Sheets

(51) Int. Cl.
   *B01L 3/00* (2006.01)
   *B01D 29/05* (2006.01)
   *C12M 1/12* (2006.01)
   *C12M 1/26* (2006.01)
   *G01N 1/40* (2006.01)

(52) U.S. Cl.
   CPC ............ *C12M 25/00* (2013.01); *C12M 33/04* (2013.01); *C12M 33/14* (2013.01); *G01N 1/4077* (2013.01); *B01D 2313/04* (2013.01); *B01D 2313/12* (2013.01); *B01D 2313/13* (2013.01); *B01D 2313/16* (2013.01); *B01D 2313/50* (2013.01); *B01L 2200/026* (2013.01); *B01L 2200/0684* (2013.01); *B01L 2200/0689* (2013.01); *B01L 2300/043* (2013.01); *B01L 2300/048* (2013.01); *B01L 2300/0681* (2013.01); *B01L 2300/0832* (2013.01); *B01L 2300/0861* (2013.01); *B01L 2300/14* (2013.01); *B01L 2400/0694* (2013.01); *G01N 2001/4088* (2013.01)

(56) References Cited

U.S. PATENT DOCUMENTS

| | | |
|---|---|---|
| 6,410,308 B2 | 6/2002 | Hendel |
| 7,546,925 B1 | 6/2009 | Zuk, Jr. |
| 8,951,788 B2 | 2/2015 | Pflanz |
| 10,184,101 B2 | 1/2019 | Pflanz |
| 2004/0063169 A1 | 4/2004 | Kane |
| 2005/0069973 A1 | 3/2005 | Bashar et al. |
| 2007/0212750 A1 | 9/2007 | Kieffer et al. |
| 2010/0028933 A1 | 2/2010 | Pflanz |
| 2015/0292995 A1 | 10/2015 | Kshirsagar et al. |
| 2021/0245106 A1 | 8/2021 | Rivat et al. |

FOREIGN PATENT DOCUMENTS

| | | |
|---|---|---|
| JP | 2001510999 A | 8/2001 |
| JP | 2004528829 A | 9/2004 |
| JP | 2020532313 A | 11/2020 |
| WO | 90/13624 A1 | 11/1990 |
| WO | 1990013624 A1 | 11/1990 |
| WO | 2008113443 A1 | 9/2008 |
| WO | 2008113444 A1 | 9/2008 |
| WO | 2014/197831 A1 | 12/2014 |

OTHER PUBLICATIONS

International Search Report dated Dec. 13, 2018 issued in corresponding PCT/EP2018/073674 application (3 pages).
Search report in corresponding Indian Application No. 202037014380 dated Mar. 21, 2022 (pp. 1-6).
Office Action in corresponding JP application 2020-513563 dated Jun. 29, 2022 (pp. 1-2).
Office Action in corresponding Columbian application NC2020/0002165 dated Jun. 27, 2022 (pp. 1-3).
Office action issued in the corresponding Japanese application No. 2020-513563 dated Apr. 4, 2023 (pp. 1-3) and english translation thereof (pp. 1-3).

* cited by examiner

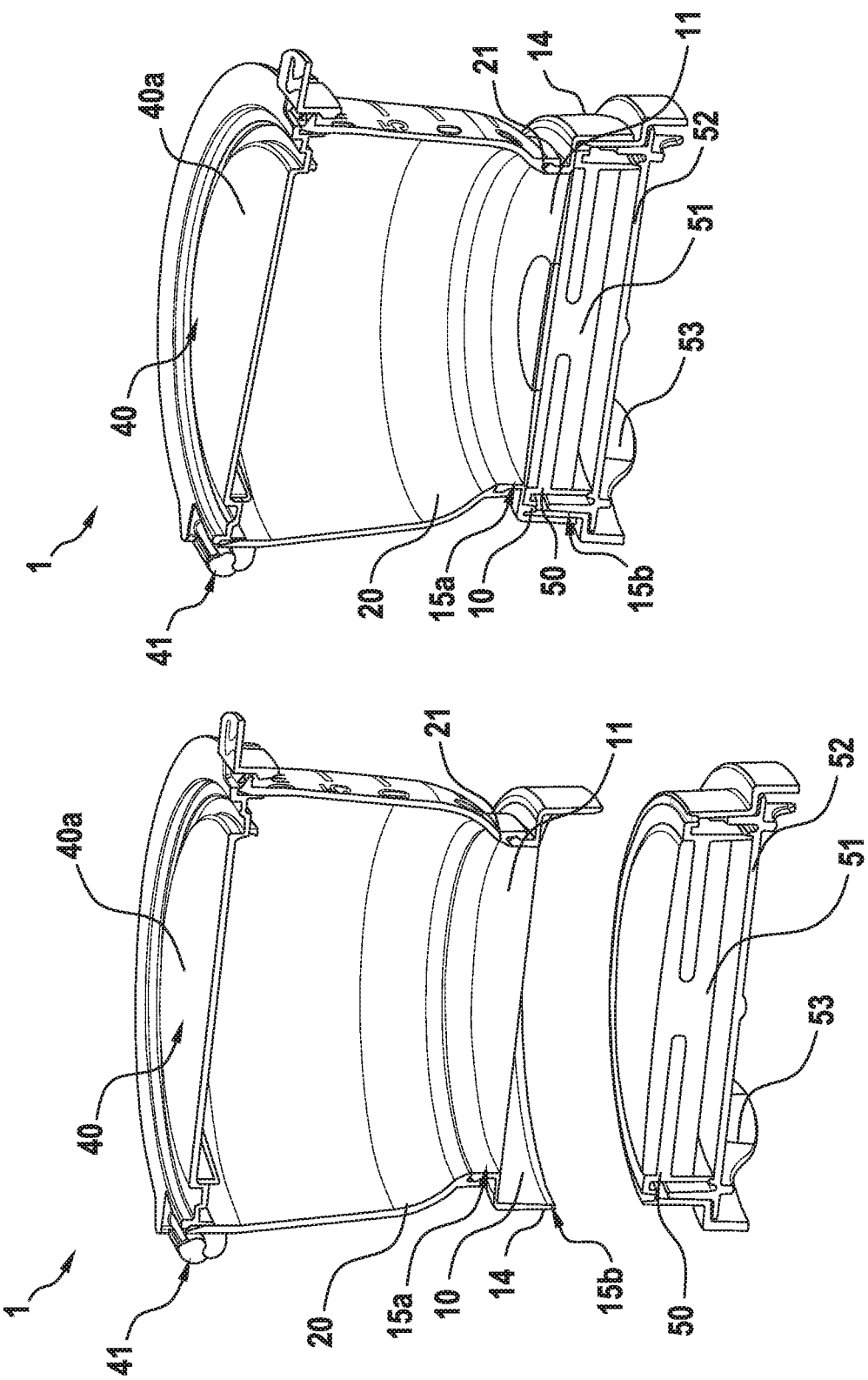

FILTRATION ASSEMBLY AND METHOD FOR MICROBIOLOGICAL TESTING

TECHNICAL FIELD

The invention concerns a filtration assembly for microbiological testing and a method of using the filtration assembly for that purpose.

Filtration assemblies are known and are frequently used for microbiological testing including sterility and bio-burden testing, for example in connection with the control of manufacturing processes or final product testing in the pharmaceutical, biopharmaceutical, biotech, hospital, food and beverage industries but also for diagnostic, health care and research and in connection with other testing tasks for particles and biological elements.

During such testing a fluid to be tested is typically passed through a filter element, e.g. a filter membrane, which is capable of capturing microorganisms of interest. After completion of the filtration process a nutrient solution that promotes the growth of the microorganisms is brought in contact with the microorganisms captured on the filter element in order to, for example with the aid of an incubator, support the growth of the microorganisms until an analyzable size of microorganism colonies is obtained.

BACKGROUND

Conventional filtration assemblies are arranged to pass the fluid to be tested through the filter element while a sub-ambient pressure or vacuum, i.e. a negative pressure, is applied on the downstream side of the filter element of the filtration assembly.

A filtration assembly disclosed in US 2004/0063169 A1 includes a cylindrical reservoir having two openings at axial ends thereof, a base having a filter support and a drainage surface for supporting a filter element and a fluid port for the fluid that has passed the filter element integrally formed with the base, and a lid removably attachable to the opening at the top axial end of the reservoir to close and fluid-tightly seal the opening. The lower opening of the reservoir is removably fluid-tightly attachable to the base so that the sample fluid passes through the filter element, is collected at the drainage surface and flows out from the fluid port. The filter element is removably supported or is permanently affixed to the base. The filter support surface may be dished, arched or wave-like in shape. After completion of the filtration process the reservoir is detached from the base and the filter element is then manually removed from the base and transferred to a petri dish in order to culture the microorganisms captured on the filter element in a nutrient solution. In an alternative mode the filter element is left atop the base and a nutrient solution is applied to an absorbent pad that has been placed beneath the filter element prior to filtration.

A filtration assembly disclosed in US 2010/0028933 A1 includes a funnel-shaped reservoir having openings at two axials ends thereof, wherein a lower end of the reservoir with the lower opening is removably attachable to a base to bring the rim of the lower opening in contact with a filter element arranged on the base. The filter element has an adhesive bond in a portion located outside the contact portion with the rim of the opening. The base has an integral draining block and a central fluid port for discharging the fluid that has passed the filter element. After filtration the reservoir is detached from the base and the filter element is lifted off from the base in that a lid with a fixing edge is brought in contact with the adhesive bond of the filter element so that the filter element adheres to the lid and then the lid is transferred to and placed on a dish-shaped separate external container formed as a petri dish or agar plate and holding the nutrient solution. During incubation the lid is retained as a cover of the external container.

A filtration assembly disclosed in WO 2014/197831 A1 includes a cylindrical reservoir with a conically more narrow top portion and an opening at the lower end, and a circular membrane holder holding a filter membrane. The top end of the membrane holder is removably and tightly attachable to the lower opening of the reservoir by means of a bayonet connector. The top end of the reservoir is closed except for an inlet connection for the sample fluid and a hydrophobic vent. The lower end of the circular membrane holder has a connection area designed to fit vacuum bars or pumps and culture media cartridges. After filtration the membrane holder is disconnected from the vacuum bar/pump, the reservoir is detached from the membrane holder, and the lower end of the membrane holder is attached to the culture medium cartridge to bring the filter membrane in contact with the nutrient solution and the upper end of the membrane holder is, if required, closed by a cap that allows incubating the sample under aerobic or anaerobic conditions—depending which side of the cap is plugged onto the membrane holder—and that makes the samples more easily stackable.

Problem to be Solved

Using the above mentioned filtration assemblies for microbiological testing requires several manual handling steps to transfer the filter element to the nutriment container or to apply the nutrient solution to the filter holder. During these steps handling errors may occur that potentially result in a contamination of the filter element (i.e. of the sample) since the filter element is more or less unprotected and unsupported (in US 2004/0063169 A1 and US 2010/0028933 A1). Moreover, due to the plurality of handling and transfer steps a series of tests cannot be repeated under exactly the same conditions.

Although a manual handling of the filter membrane or of the nutrient solution is avoided with the filtration assembly disclosed in WO 2014/197831 A1 since the filter membrane is retained in the circular membrane holder during the filtration and incubation steps, the filtration procedure and microorganism concentration and collection on the membrane is inferior and subject to considerable variation from one test to the other because the assembly has no drain member underneath the filter membrane.

Since handling errors or imprecision during bioburden testing may require long and costly investigations, it is an object of the present invention to provide a cost effective filtration assembly that may be simply and intuitively operated in a clear and transparent sequence of steps to avoid handling mistakes, that is capable of avoiding external contamination and that secures a high reproducibility and comparability of test processes and test results.

Means for Solving the Problem

To solve the problem, the present invention provides a filtration assembly as defined in claim 1, and a method of filtrating a sample fluid as defined in claim 14. Preferred embodiments of the filtration assembly and of the method of filtrating are defined in the dependent claims.

A filtration assembly for microbiological testing according to the present invention comprises a ring-like membrane support holding a filtration membrane, a cylindrical reservoir of which opposite axial ends have openings and one axial opening is removably and fluid-tightly attachable to the membrane support to define a sample volume adjacent to the filtration membrane on one axial side of the membrane support, and a drain member removably and fluid tightly attachable to the membrane support to define a drain channel space adjacent to the filtration membrane on an opposite axial side of the membrane support.

Since the drain member is connected with the membrane support it can be transferred to a pump head or vacuum bar in one single step or operation. The drain member secures an improved drainage management, an improved membrane drying and a reproducible microorganism colony repartition by controlling the negative pressure applied on the membrane and directing the deposition of microorganisms on the membrane. After filtration the membrane support with the membrane can be pulled off from the pump head or vacuum bar leaving the drain member held by the head or bar. Moreover, since the drain member and the reservoir are both removable from the membrane support, the membrane is fully accessible from both axial sides of the membrane support while the membrane remains held by the membrane support during the entire filtration process and is protected from unintentional contact with equipment and contamination sources.

Preferably the filtration assembly further comprises a lid device removably and fluid tightly attachable to the other axial opening of the reservoir to close the opening, wherein the lid device is removably and fluid tightly attachable to the membrane support so as to seal the one axial side of the membrane support from the environment.

In this preferred embodiment the lid device may be selectively attached to both the membrane support and the reservoir and can be used in the filtration process up to and including the step of filtration and can again be re-used in the step of incubation. This reduces the number of different elements in the filtration assembly. When attached to the membrane support or the reservoir a plurality of membrane supports or reservoirs each having the lid attached thereto may be stacked on one another. Further, the membrane is protected from being damaged or polluted from the axial side where the lid is attached. In addition, the lid may secure defined conditions during the incubation process.

Preferably, the lid device has a hinge for supporting a lid portion so as to allow selective opening of the lid device in a predefined movement.

Due to the provision of the hinge the lid portion may be opened in a predefined articulated manner and guided to several distinct positions while the lid portion remains attached to either the membrane support or to the reservoir. This avoids inadvertent falling off of the lid portion or contamination during handling because the user does not have to temporarily place the lid separate from the assembly. Further, the user always has both hands free to perform other operations.

Preferably, the hinge is included in the lid device. A part of the hinge may be provided on the reservoir and/or on the membrane support and the other part of the hinge may be provided on the lid device. Where the entire hinge is provided on the lid device the reservoir and the membrane support can have a simple and universal structure without including components of the hinge. This allows retrofitting of existing designs with the lid device including all elements required for the articulation of the lid portion. If the articulated parts of the hinge are separable, the attaching position of the lid device is predefined and the structure of the lid device can be simplified.

Preferably, the hinge of the lid device is formed so as to provide at least three defined positions of the lid portion including one where the lid portion seals, i.e. fluid-tightly closes the opening, one where the opening is accessible and the lid portion is preferably restricted by a mechanical stopper, and one where the lid portion closes the opening but allows a defined venting into the opening.

Accordingly, a stable open position for sample filling into the reservoir and a stable venting position are secured and can be intuitively set by the user. In the defined position that allows the venting the opening of the reservoir or membrane support is closed and protected from external contaminants but remains vented with no risk of accidental closure, e.g. during the vacuum filtration step. The provision of the mechanical stopper defines the proper opening position of the lid portion for filling the reservoir and/or access to the filter membrane.

Preferably, the drain member is removably attachable to the membrane support by frictional and/or form-locking engagement, preferably by a snap-fit engagement.

Accordingly, the drain member can be easily detached from and attached to the membrane support with a predefined force or motion, thereby avoiding unintentional separation of the two elements.

Preferably, the drain member is received in a skirt portion surrounding the opposite axial side of the membrane support. With this structure the drain member is protected from external contact and can be removed in that the drain member is being held by the pump or vacuum bar at the end of the filtration step while the membrane support is separated from the drain member and transferred to the incubation step without the drain member.

Preferably, the drain member comprises a collecting surface facing the membrane for collecting fluid having passed the membrane formed on the membrane support, wherein the collecting surface is preferably concave with an apex spaced apart from the membrane when the drain member is attached to the membrane support, one or more radial flow channel(s) formed on the collecting surface, and a discharge port for discharging the fluid collected on the collecting surface to a side opposite to the collecting surface.

The concave collecting surface of the drain member allows the membrane to be supported uniformly and substantially throughout its entire surface when the membrane is wet, i.e. after the filtration has begun. This avoids fold formation in the membrane created by membrane dilatation due to a so called "swallowing effect" since the membrane can expand downward. The concave shape with the apex spaced apart from the central portion of the dry membrane allows the membrane to assume a convex bulge or bump when a slight overpressure in the reservoir is created. This convex bulge or bump of the membrane in the central portion in return provides advantages when the membrane support with the membrane is attached to a media cassette with a nutrient medium described later because it allows the membrane to preferentially come in contact with the nutrient medium in the center and a subsequent radial pushing and expansion of the contact zone in order to avoid trapping of air bubbles between the membrane and the nutrient medium. Further, the radial fluid flow channels evenly distribute the fluid that has passed the membrane over the surface of the membrane and guide the fluid to the central discharge port.

Preferably, the drain member further comprises a venting opening penetrating the drain member from the side opposite to the collecting surface to the side of the collecting surface to allow ambient air to be supplied to the collecting surface, preferably via a circular air groove formed on the surface of the drain member facing the membrane and surrounding the collecting surface and in communication with the radial flow channel(s) thereof.

By providing the venting opening in communication with the radial flow or distribution channel(s) via the circular air groove the drainage of the fluid and the drying process of the membrane are improved since the region between the membrane and the drain member may be selectively purged with air supplied through the venting opening during or at the end of the filtration step.

Preferably, the collecting surface of the drain member has a smaller radius than the membrane held in the membrane support and is spaced from an outer circumference of the membrane.

This configuration provides the advantage that the microorganisms are captured and concentrated in a portion of the membrane that is sufficiently spaced from the peripheral junction between the membrane and the membrane support to thereby avoid the risk of annular microbial spreading. It also helps concentrating the microorganisms to the portion of the membrane that will be preferentially brought in contact with the nutrition medium in the media cassette to be described later.

Preferably, the reservoir is removably attachable to the membrane support by frictional and/or form-locking engagement, preferably by a snap-fit connection.

Accordingly, the reservoir can be intuitively and easily detached from and attached to the membrane support and both elements can be handled as a unit.

Preferably, the cross-sectional area defining the sample volume of the reservoir, perpendicular to the axial direction of the reservoir, gradually increases at least in a portion adjacent to the opening of the reservoir to be attached to the membrane support, towards the other opening of the reservoir. Further preferably, the reservoir has a lip portion with an acute tip end protruding radially inward at the opening of the reservoir to be attached to the membrane support.

Accordingly, due to the at least partially conical or rounded restriction of the cross section of the reservoir towards the lower opening the fluid to be tested can evenly flow towards the membrane. Further, droplet formation at the lower end side of the reservoir is avoided when the reservoir is separated from the membrane support, especially in conjunction with the acute protruding tip end of the lower end of the reservoir, so that contamination of the membrane and/or of the surrounding workplace is prevented when the reservoir is detached from the membrane support.

Preferably, the filtration assembly further comprises a media cassette configured to hold a nutrient medium, wherein the media cassette is removably and air-tightly, preferably by a frictional and/or form-locking engagement, attachable to the membrane support at the side where the drain member is to be attached but with the drain member being not attached, such that the membrane can get in contact with the nutrient medium.

The provision of the media cassette that is attachable to the membrane support renders the filtration assembly suitable for performing the entire filtration process including the incubation phase with the assembly having a minimum number of compatible components. There is in particular no need to manually handle or remove the membrane as such, e.g. with tweezers, to transfer it to an incubation container like a petri dish in order bring it in contact with a nutrient medium since the membrane holder (i.e. the membrane support) with the membrane remaining attached to it is combined with the media cassette. Therefore, the risk of contamination of the membrane or of errors in handling of the membrane are reduced or prevented. Further, since the drain member is detachable from the membrane support before the membrane support is attached to the media cassette, the entire lower surface of the membrane is accessible and can be exposed to the nutrient medium.

Preferably, a nutrient medium, preferably an agar nutrient, is disposed inside the media cassette so as to have an upward bulge in a central portion and so as to preferentially come in contact with a central portion of the membrane when the media cassette is attached to the membrane support.

Accordingly, the central upward bulge or bump of the nutrient medium in the media cassette further supports the effect that the nutrient medium following the initial contact with the—preferably downward bulged central portion of the membrane—is pushed radially outward towards the periphery of the media cassette by the progressing contact zone with the membrane during the attaching process of the membrane support to the media cassette. Thereby, the inclusion of air bubbles between the membrane and the nutrient medium is avoided and a sufficient contact area between the membrane and the nutrient medium is secured.

A method of filtrating a fluid using the filtration assembly of the invention including the media cassette comprises the steps of:

preparing the filtration assembly such that the one opening of the reservoir is attached to the one axial side of the membrane support, the lid device is attached to the other opening of the reservoir, and the drain member is attached to the other axial side of the membrane support, mounting the other side of the membrane support with the drain member on a suction device, filling an amount of fluid to be filtrated into the sample volume of the reservoir, moving the lid portion into the position so as to allow a defined venting, operating the suction device until a desired amount of the fluid has passed through the membrane, removing the drain member from the membrane support, attaching the membrane support to the media cassette such that the membrane comes in contact with the nutrient medium, removing the reservoir from the membrane support and removing the lid device from the reservoir, re-attaching the lid device to the opening of the media cassette, and moving the lid portion of the lid device into the position so as to allow a defined venting or as to seal the opening of the media cassette.

The method of filtrating a fluid preferably further comprises the following steps during the step of operating the suction device:

moving the lid into the position where it seals the other opening of the reservoir, and allowing ambient air to pass into a space between the membrane and the collecting surface of the drain member to allow drying the membrane.

Since there is no need to manually handle and transfer the membrane as such after filtration, and since the drain device is removed from the membrane holder before the membrane holder is attached to the media cassette for incubation, the entire process can be intuitively and safely performed with an improved reproducibility and repeatability of the testing conditions without errors, with a high yield of microorganism capture and growth on the membrane and with a reduced risk of contamination.

The drying of the membrane by the particular venting of the space between the membrane and the drain member before the membrane it is brought in contact with the nutrient medium further improves and accelerates the growth of the microorganisms.

BRIEF DESCRIPTION OF THE DRAWINGS

Preferred embodiments of the filtration assembly according to the present invention will be described by reference to the attached drawing, in which:

FIG. 11 is a perspective view showing the membrane support with the reservoir but without the drain device before and after attachment to the media cassette.

DETAILED DESCRIPTION OF THE EMBODIMENTS

Figure 1:
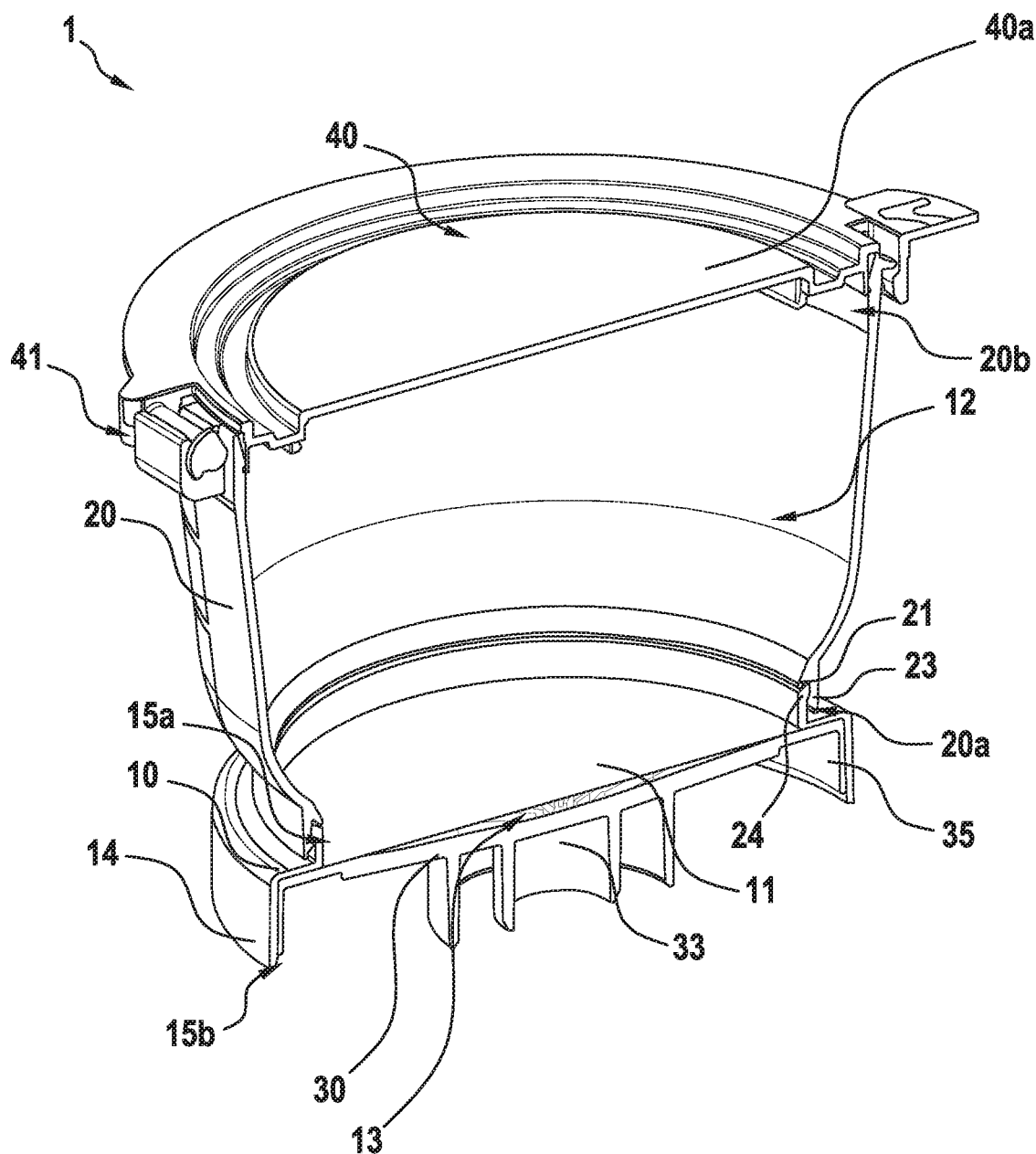
FIG. 1 is a perspective sectional view from a top showing a filtration assembly according to an embodiment.
Figure 2:
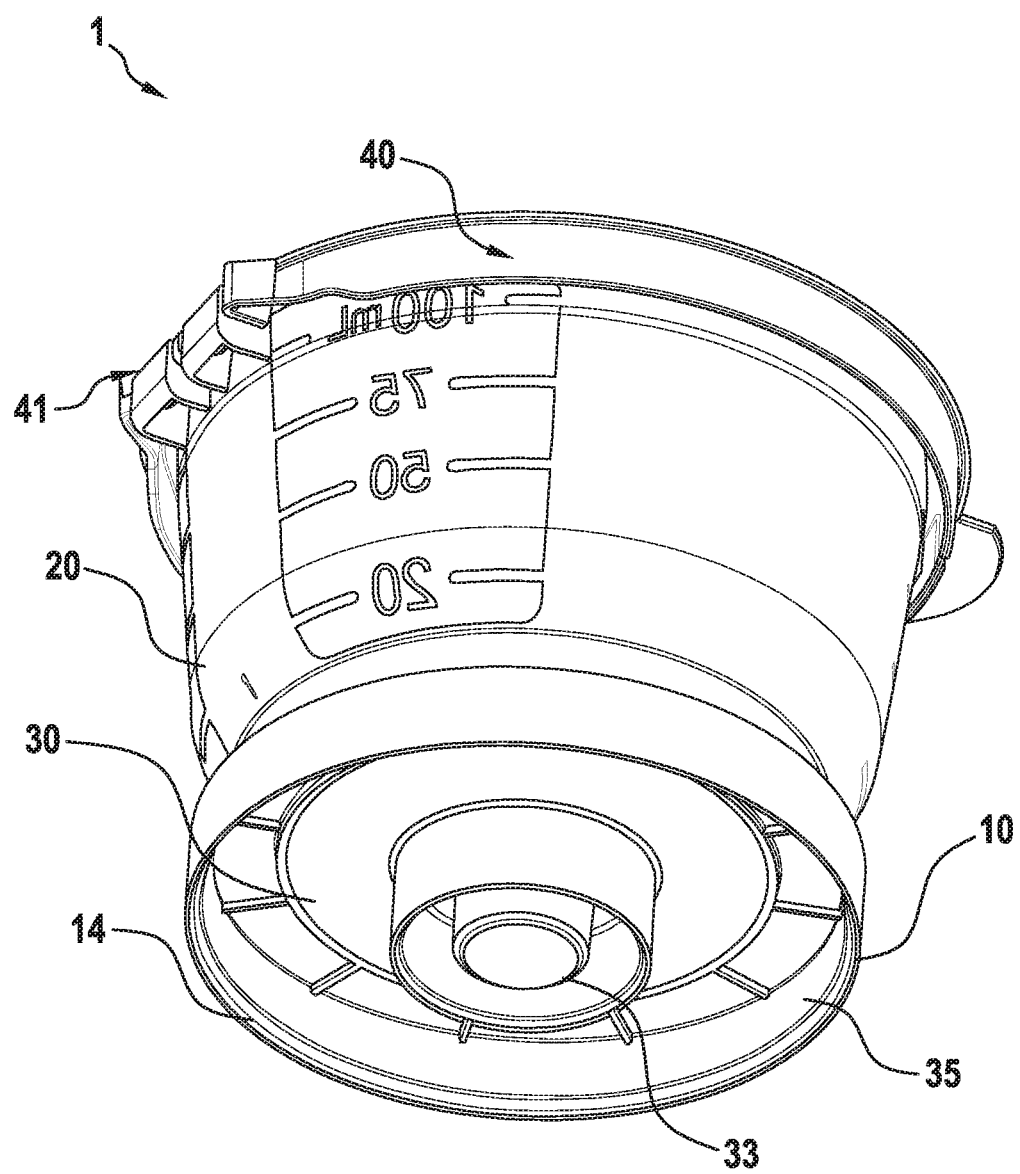
FIG. 2 is a perspective view from a bottom showing the filtration assembly according to the embodiment.

A filtration assembly 1 according to an embodiment of the present invention is shown in a schematic perspective representation viewed from top and bottom in FIG. 1 and FIG. 2. The filtration assembly 1 of the present invention comprises a ring-like membrane support 10 holding a filtration membrane 11, a cylindrical funnel-like reservoir 20 of which opposite axial ends have openings and one axial opening thereof (the lower opening) is removably and fluid-tightly attachable to one side of the membrane support 10 to define a sample volume 12 adjacent to the filtration membrane on one axial side of the membrane support 10, and a drain member 30 removably and fluid tightly attachable to the membrane support 10 to define a drain channel space 13 adjacent to the filtration membrane 11 on an opposite axial side of the membrane support 10.

The membrane support 10 is shaped like a ring including a peripheral skirt 14 defining openings 15*a*,15*b* at axial sides thereof. The skirt 14 has a stepped profile in a cross section through a plane including a central axial direction so that the top opening 15*a* has a smaller diameter than the bottom opening 15*b*. The stepped profile is, however, not an essential aspect and the skirt can be continuous on the outer periphery or can have any other shape or structure.

The membrane support 10 is a self-supporting member and is adapted to hold the membrane 11 in a flat orientation in that the membrane is fixed to the membrane support by, for example, clamping-means, adhesive, fastening means like pins or screws, or a combination thereof. The membrane can also be clamped between two members forming the membrane support or can be integrally molded into the material of the membrane support at an outer periphery thereof. Moreover, the membrane support 10 may include an element like a mesh to additionally mechanically support the membrane 11 in the flat orientation.

The membrane 11 is normally incorporated into the membrane support 10 during manufacturing but the membrane support 10 can be designed such that the membrane 11 is attached to the membrane support 10 at the point of use. The membrane 11 may be a conventional single or multilayer filter membrane capable of capturing the microorganisms of interest.

The reservoir 20 may have any structure which enables it to hold a desired volume of a sample fluid which is to be tested with the assembly. In the illustrated embodiment, the reservoir 20 is generally cylindrical and funnel-shaped with the diameter increasing towards the top of the reservoir 20 in the normal vertical orientation during use and it has openings 20*a*,20*b* at its axial upper and lower ends. Further, the reservoir 20 may have additional chambers (not shown) for holding, for example, a substance required for the sample preparation process. The reservoir 20 may be partly or completely transparent to allow monitoring the sample fluid in the sample volume 12 and the process from outside.

The outer peripheral wall of the reservoir 20 defining the sample volume 12 may include markings on its inner and/or outer wall surfaces to assist a user in determining the amount of sample fluid received by the reservoir 20.

An inner diameter of the inner wall surface may vary over at least a portion of the height of the reservoir 20 adjacent to the lower opening 20*a* that is intended to be attached to the membrane support 10 such that the cross sectional area of the reservoir 20 perpendicular to the axial direction thereof gradually increases from the lower opening 20*a* of the reservoir 20 towards the top opening 20*b* at the other axial end of the reservoir 20. Preferably, the increase of the sectional area of the sample volume 12 is linear (i.e. so that the cross-section profile is conical) or non-linear (i.e. so that the cross section profile is rounded) or is any combination of the two. In other words, the inner wall of the reservoir 20 is inclined and funneled radially inward, i.e. toward the vertical axis of the reservoir 20, at least at a downstream part of the reservoir 20 in order to create a flow of the fluid towards the membrane 11. Nevertheless, the inclined shape of the inner wall surface of the reservoir 20 may also be provided throughout the height of the reservoir 20.

Figure 6A:
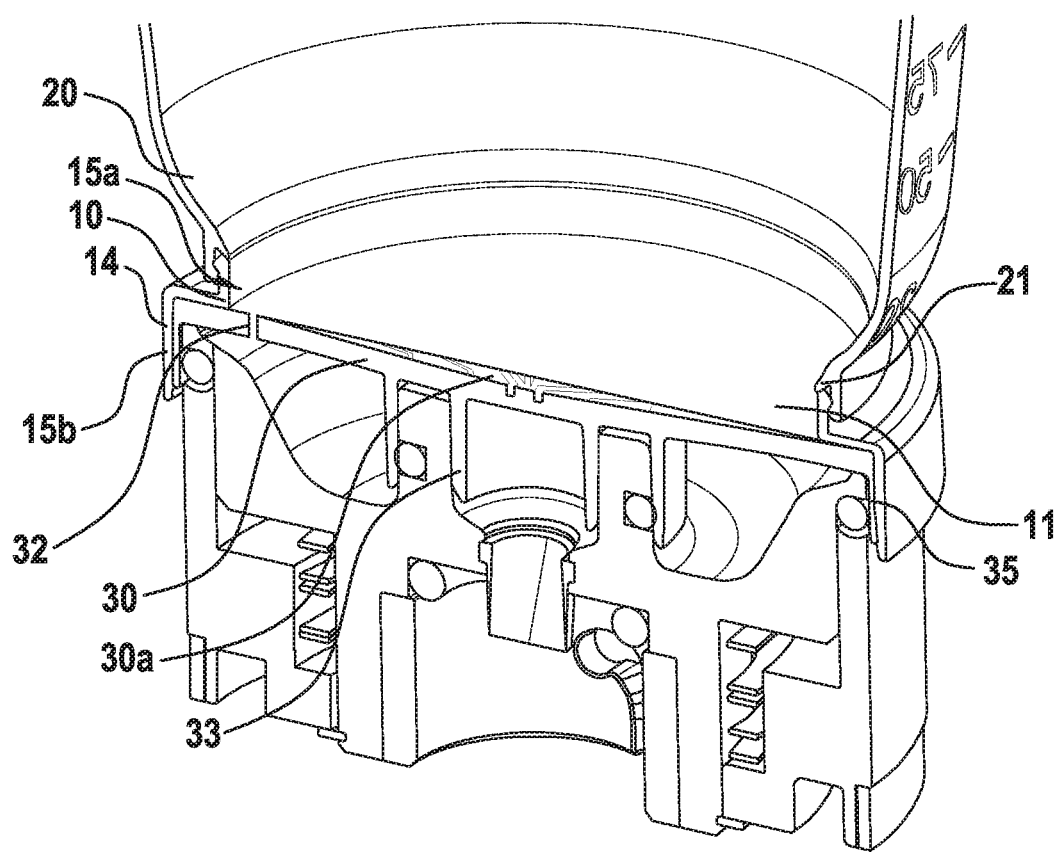
FIG. 6A is an enlarged perspective sectional view showing a part of the filter assembly according to the embodiment when mounted on a suction device during the filtration step.

According to a preferred embodiment as shown in FIG. 6A for example the reservoir 20 has a lip portion 21 with an acute tip end protruding radially inward at the lower opening 20*a* of the reservoir 20 to be attached to the membrane support 10 so as to cover an upper end of a snap-fit connection 22 between the reservoir 20 and the membrane support. In combination with the snap-fit connection 22 being formed so that an engagement rim or protrusion 23 of the reservoir 20 is located on the radial outside whereas the corresponding engagement rim or protrusion 24 of the membrane support 10 is located on the radial inside of the snap-fit connection 22 this configuration avoids the formation of droplets when the reservoir 20 is detached from the membrane support 10.

The snap-fit connection 22 between the reservoir 20 and the membrane support 10 is an example of a removable fluid-tight and air-tight frictional and/or form-locking attachment but other connections between the reservoir 20 and the membrane support 10 like a bayonet fit, a threaded engagement, a press fit or a connection using a fastener or clamp are possible if they are releasable by a user, create a sufficiently rigid and strong connection that allows the intended handling and transport of the combined elements as a unit during the filtration process without unintended separation, and provide a supply of the fluid from the reservoir 20 to the membrane support 10 such that leaking out of the fluid is prevented.

The drain member 30 is designed to be removably, fluid-tightly and air-tightly attached to the membrane support 10 during manufacturing or at the point of use such that all the fluid to be filtered passes though the filtration membrane 11 and is collected by the drain member 30 and is directed to a discharge port 33 while leaking out of the fluid especially through the connection portion between the drain member 30 and the membrane support 10 is prevented. The drain member 30 is removably attachable to the membrane support 10 by frictional and/or form-locking engagement, such as by a bayonet fit, threaded engagement, press fit or a snap-fit engagement. Preferably the drain member 30 has an outer skirt 35 that is inserted and concentrically held inside the skirt portion 14 of the membrane support 10. The skirt portion 14 of the membrane support 10 and the skirt 34 of the drain member 10 may comprise engagement features configured to establish the desired fluid-tight releasable connection between the membrane support 10 and the drain member 30 that permits both a sufficient support (avoiding an unintentional separation) and a selective separation of the two elements in the filtration process as described further below.

When the drain member 30 is attached to the membrane support which in return is attached to the reservoir to form a self-supporting unit, the drain member 30, especially the skirt 35 and the discharge port 33, is configured to be connected to a head of a suction device/pump or vacuum bar that is known in the art in order to apply a vacuum or negative pressure to the downstream side of the membrane 11 such that the sample fluid initially received in the sample volume 12 of the reservoir 20 adjacent to the upstream side of the membrane 11 is urged to pass through the membrane 11 and is collected in a collecting surface 30a formed on the membrane support 10 so as to face the membrane 11 for collecting fluid having passed the membrane 11. The collecting surface 30a is preferably concave with an apex or bottom on the central axis of the membrane support 10 aligned with the discharge port 33 but initially spaced apart from the membrane 11 when the drain member 30 is attached to the membrane support 10. The collecting surface 30a has a pattern of one or more radial flow channel(s) 31 formed on the collecting surface 30a so as to distribute and direct the fluid towards the discharge port 33 through which the fluid is discharged to a side opposite to the collecting surface 30a.

The concave collecting surface 30a of the drain member 30 can support the central portion of the membrane 11 in a wetted state in addition to the peripheral portion of the membrane 11 remaining held at the membrane support 10. That is, when the membrane 11 is hydrated, it expands from the flat state and approaches the concave collecting surface 30a due to dilatation. The concave collecting surface 30a can thus accommodate the larger dimensions of the membrane 11 and can prevent the formation of folds in that the membrane 11 can evenly lay on the concave surface 30a (hereinafter also referred as concave surface or collecting surface).

Figure 8:
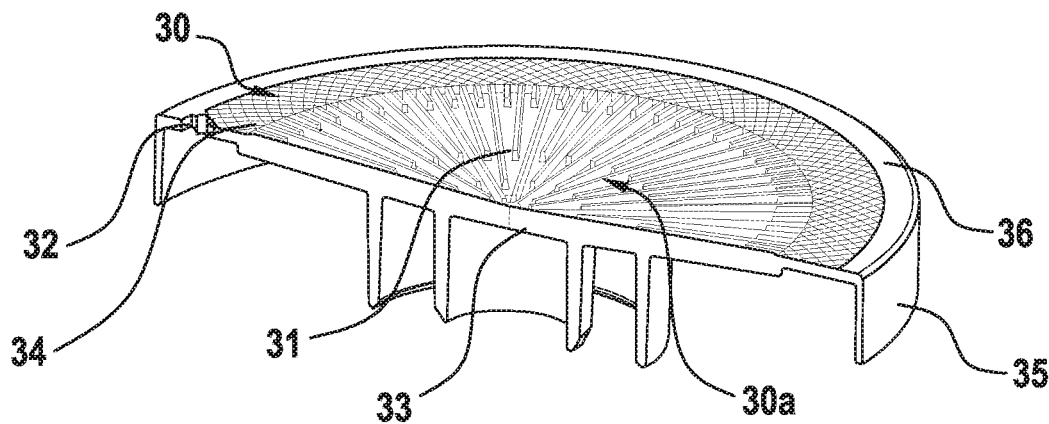
FIG. 8 is perspective sectional view showing a drain member of the filtration assembly according to the embodiment.
Figure 9:
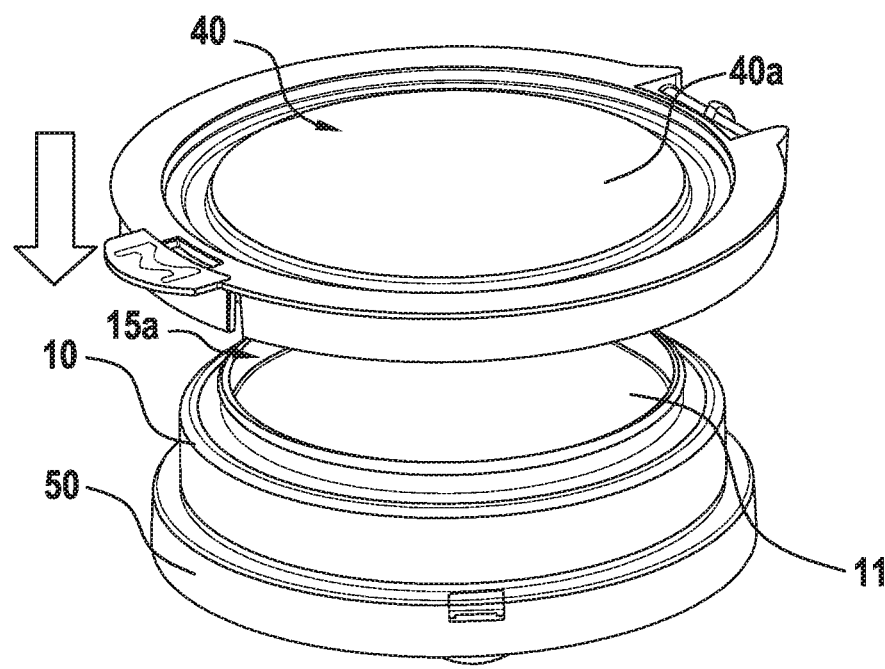
FIG. 9 is a perspective view showing a membrane support of the filtration assembly having a lid device attached to an axial side thereof.

As shown in FIG. 8 the concave surface 30a is provided with a pattern of a plurality of radial flow channels 31 which are regularly distributed over the concave surface 30a. The radial flow channels 31 may be formed as recesses from the concave surface 30a defined by the raised portions of the surface and they receive and guide the fluid that has passed through the membrane 11 towards the discharge port 33. Preferably, the discharge port 33 is disposed at the centre of the drain member 30 and is configured to be air-tightly connected to the suction device in order to apply the negative pressure to the space downstream of the membrane 11 defined by the concave surface 30a including the flow channel(s) 31.

Further, one or more venting hole(s) or opening(s) 32 are formed in the drain member 30 at a radial outer position so as to penetrate the drain member 30 from one axial side of the drain member 30 to the other side and through which ambient air can be supplied to a circular air groove 34 which is formed on the surface of the drain member 30 facing the membrane 11 when the drain member 30 is attached to the membrane support 10, and which is also in communication with the radial flow channel(s) 31.

The venting opening(s) 32 is/are configured to deliver ambient air to the circular air groove 34 which is arranged to surround the collecting surface 30a in which the radial flow channel(s) 31 is/are disposed. The venting opening(s) 32 is/are such that, while the negative pressure is applied to the downstream side of the membrane 11 via the discharge port 33 connected to the vacuum pump, an air-tight connection between the head of the pump and the outer peripheral skirt 35 of the drain member 30 that is normally established during the filtration process is temporarily selectively released so that ambient air can pass between the skirt and the head to the side of the drain member 30 opposite to the side having the collecting surface 30a and from there through the venting opening(s) 32 to the collecting surface 30a.

The ambient air delivered through the venting opening 32 to the circular air groove 34 is subsequently distributed to the radial flow channels 31 and sucked to the discharge port 33 and discharged towards the suction device. The air passing along the downstream surface of the membrane 11 dries the membrane 11 and discharges a potentially remaining rest of fluid trapped between the membrane 11 and the drain member 30 to the discharge port 33 in order to purge the region between the membrane 11 and the membrane support 30 after the filtration process (see FIG. the two small arrows in 6B schematically indicating the ambient air flowing through the venting opening 32). The purging effect may be further enhanced by preventing air supply from the side of the sample volume, for example by sealing the top opening of the reservoir 20 by means of the lid device to be described later.

Preferably, the collecting surface 30a of the drain member 30 has a smaller radius than the membrane 11 held in the membrane support 10 and is spaced from an outer circumference of the membrane 11 where the membrane 11 is joined with the membrane support 10, thereby leaving a certain peripheral zone 36 without fluid channels. The circular air groove 34 and the radial flow channel(s) 31 are provided in a portion of the drain member 30 and the air groove 34 delimits the outer periphery of the collecting surface 30a. As a result, the microorganisms potentially contained in the fluid filtered through the membrane 11 are captured and mainly concentrated on the region of the membrane 11 corresponding to the collecting surface 30a and are sufficiently spaced from the peripheral edge of the membrane 11.

In a further alternative embodiment, additionally or alternatively to the radial flow channel(s) 31, the collection surface 30a can be provided with individual dimples or indentations which are distributed in various patterns about the concave surface, or with further annular grooves, preferably in concentric arrangement, or with combinations thereof.

As mentioned above, the connection between the drain member 30 and the membrane support 10 is releasable and it is furthermore configured such that, when the filtration assembly 1 is held on the head of the vacuum pump or vacuum bar (suction device) via the drain member 30, the rest of the filtration assembly 1 comprising the membrane support 10 and the reservoir 20 attached together can be detached from the suction device as a unit while the drain member 30 remains attached on the suction device in that the drain member 30 is separated from the membrane support 10.

In a particularly advantageous structure the filtration assembly 1 comprises a lid device 40 removably and fluid tightly attachable to the top axial opening 20b of the reservoir 20 to close the opening. The lid device 40 is configured to be also removably fluid tightly attachable to the membrane support 10 so as to seal the one (top) axial opening 15b of the membrane support 10 from the environment. This can be realized in that the top openings 20b, 15b of the reservoir 20 and the membrane support 10 have substantially the same dimensions and configuration of a rim or edge surrounding them that can engage with a mating recess of the lid device 40 to effect the seal, or in that the configuration and/or dimensions of the rims surrounding the openings 20b, 15b are different but the lid device 40 has two mating recesses respectively sized and arranged to respectively engage with one of them.

In the embodiment the lid device 40 is shaped and provided with a recess that is configured so as to be detachably arranged atop the rim surrounding the opening 20b at the top axial end of the reservoir 20. The lid device 40 may engage with the top end of the reservoir 20 in various manners including a snap fit, a bayonet fit, a threaded engagement, or a press fit or a loose fit combined with a holding device. The engagement provides in any case the possibility of a substantially air tight seal between the lid device 40 and the reservoir 20, and the engagement is such that it provides sufficient resistance to inadvertent disengagement of the lid device 40 from the reservoir 20 or the top opening 15b of the membrane support 10 during handling and transport before and during filtration and incubation and analysis procedures (i.e. when the lid device 40 and the support member 10 together are used as an incubation container).

Preferably, the lid device 40 has a hinge 41 for supporting a lid portion 40a (that is the part provided with the respective recesses described above) so as to allow selective opening of the lid device 40 in a predefined movement. In other words, the lid portion 40a of the lid device 40 is articulated to either one or both of the reservoir 20 and the membrane support 10 when attached. Additionally, the lid device 40 is provided with a lid-lock to prevent the lid portion 40a from being accidently opened. The lid lock may be provided by engagement of two complementary engaged portions formed on the lid device 40 and the reservoir 20 (and/or the membrane support 10) that can be disengaged only if a certain force or motion is applied.

According to an embodiment of the present invention the entire hinge mechanism 41 is included in the lid device 40 which in return can be attached, i.e. as a snap-fit or other releasable connection, to the reservoir/membrane support as a functional unit. That is, the reservoir 20 and/or the membrane support 10 in this case do not need the complementary element for articulating the hinge and can be thus of simple design.

According to another embodiment that is shown in the drawing one part of the hinge mechanism 41 is provided on the reservoir 20 and/or on the membrane support 10 and the other part of the hinge mechanism 41 is provided on the lid device 40. That is, complementary parts for the articulation of the hinge are provided on the lid 40 and the reservoir 20 and/or on the membrane support 10. These complementary parts may be in the form of a simple articulated joint with a protrusion inserted into a mating recess and defining a rotation axis that is located in a plane perpendicular to the central axis of the filtration assembly and preferably substantially tangential to the respective opening to be closed by the lid device 40.

Figure 3A:
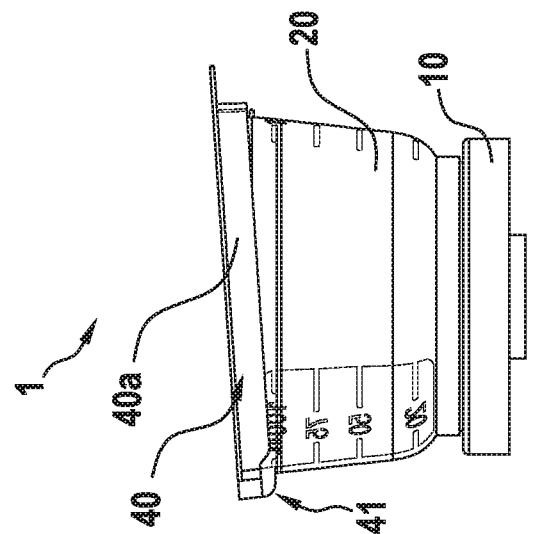
FIG. 3A-3C are side views showing the filtration assembly according to the embodiment having a lid portion in three different defined postures.
Figure 3B:
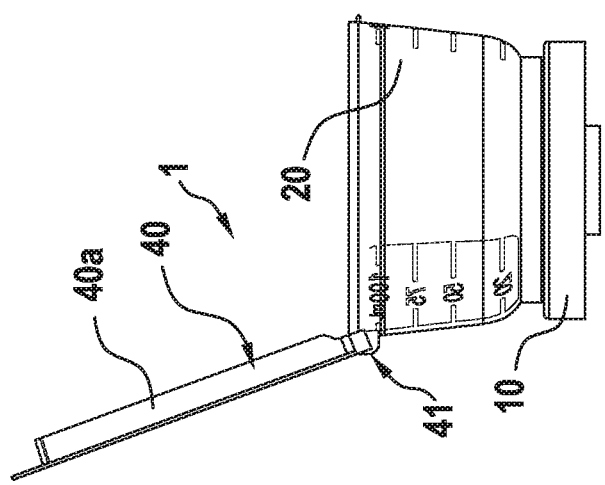
Figure 3C:
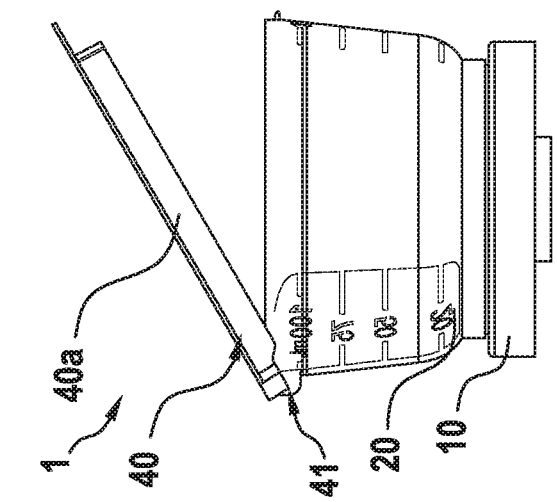

Independent from the location and structure of the hinge mechanism 41 the lid device 40 is preferably formed so as to provide at least three defined positions of the lid portion 40a shown in FIGS. 3A to 3C including one where the lid portion 40a seals the opening (fluid-tightly), one where the opening is accessible and the lid portion 40a is at its most open state, preferably restricted by a mechanical stopper, and one where the lid portion closes the opening to prevent ingress of any particles or contaminants but allows a defined venting into the opening.

Additional positions of the lid portion 40a such as one position in which the lid portion 40a in the open state encloses a particular angle, for example of substantially 45 degrees, with the horizontal plane (see FIGS. 3A, 4A and 4B) are possible.

Figure 4B:
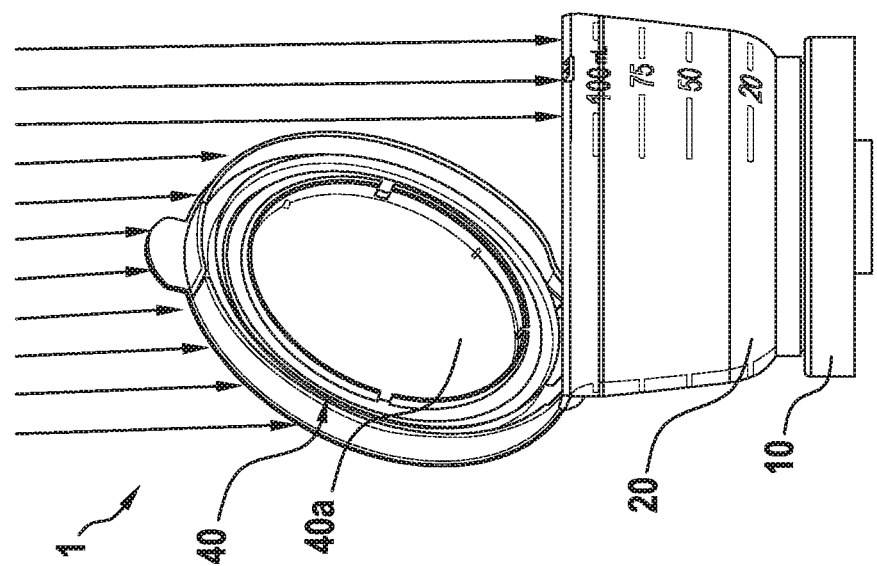
FIG. 4B is a side view showing the filtration assembly according to the embodiment having the lid portion in the defined posture.
Figure 4A:
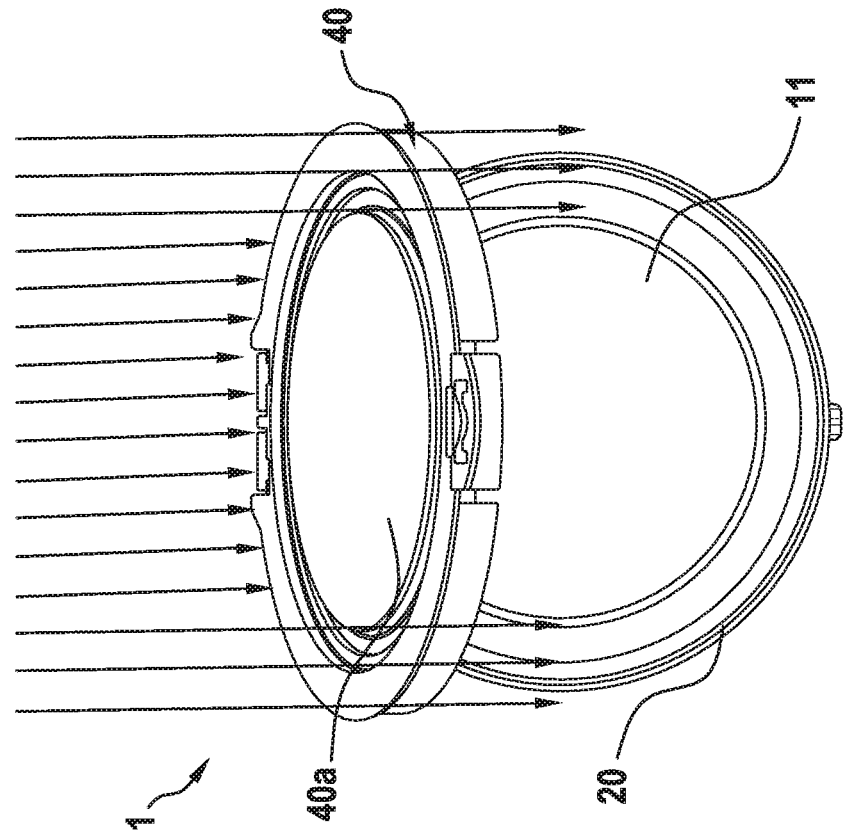
FIG. 4A is a top view showing the filtration assembly according to the embodiment having the lid portion in a defined posture.
Figure 5A:
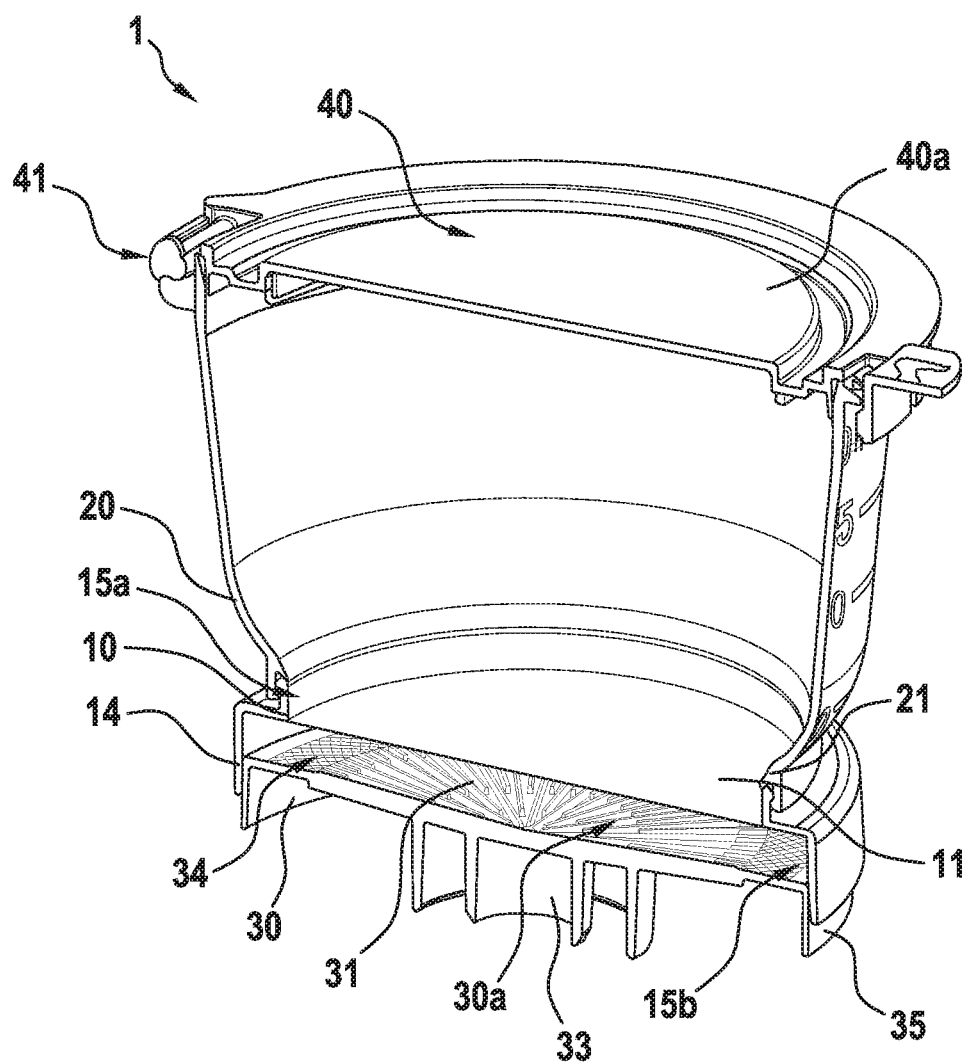
FIG. 5A is a perspective sectional side view showing the filtration assembly according to the embodiment.
Figure 5B:
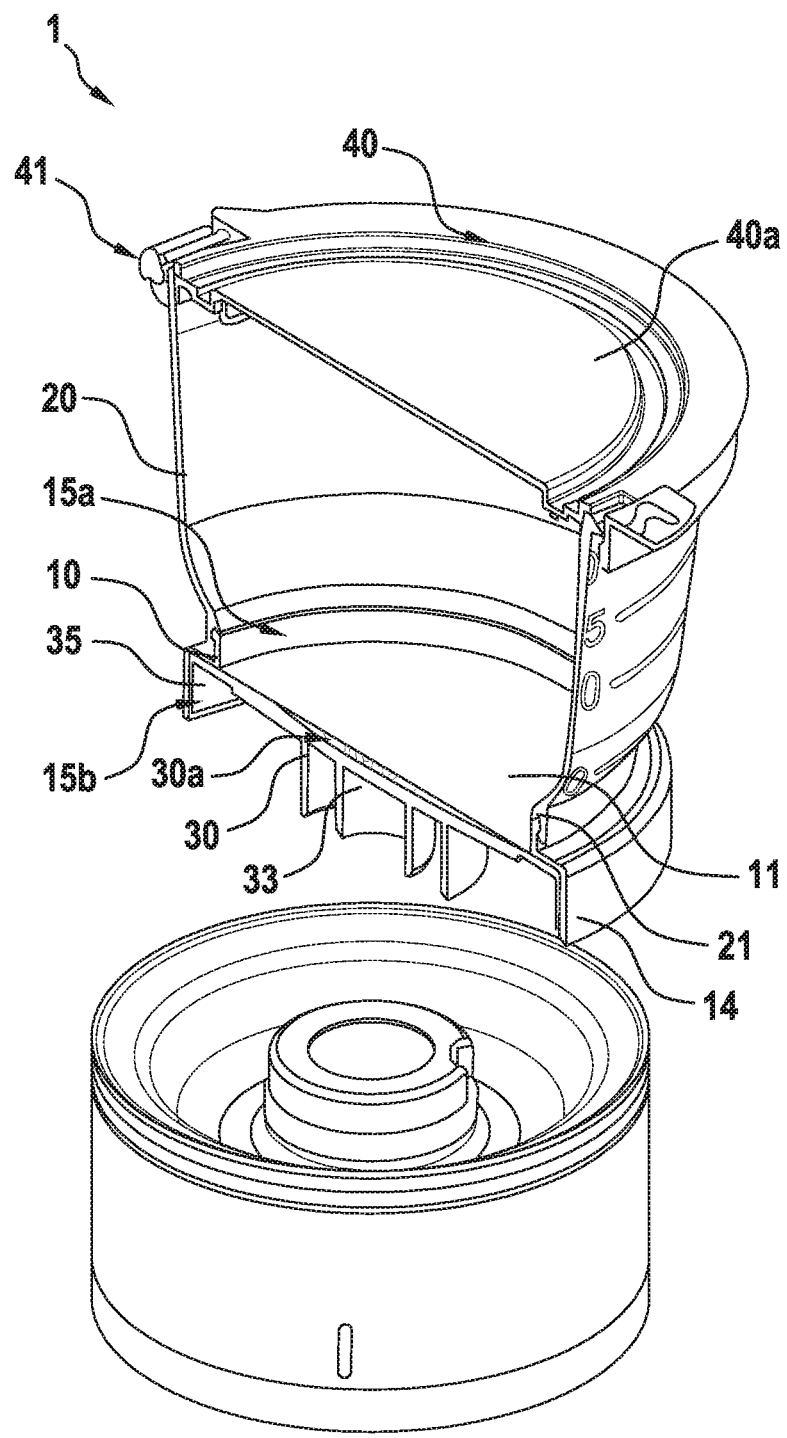
FIG. 5B is a perspective sectional view of the filtration device of FIG. 5A before it is transferred to a pump head of a vacuum pump.

When the lid portion 40a is held in a position that allows the user to access the volume 12 of the reservoir 20, e.g. in which the lid portion 40a encloses an angle of 90 degrees or less with the horizontal plane, there is the advantage that, when the filtration assembly 1 is used within a clean room (for example within a conventionally known "clean bench"), the risk that a contaminant enters the opening (of the reservoir or the support member) at which the lid device 40 is arranged is significantly reduced since the inclined lid portion 40a shields a part of the opening and thus prevents a substantial portion of the purified air flow produced in the working zone inside the clean bench and directed in a vertical direction and/or in a horizontal direction from entering directly into the filtration assembly 1 (see parallel arrows in FIG. 4A and FIG. 4B). In addition, the inside of the clean bench can have a slight overpressure as compared to the environment outside of the clean bench.

The stopper for the maximum opening can be a mechanical stop, e.g. a protrusion provided on either the lid device 40 or the reservoir/membrane support or both, that blocks further movement in the pivoting direction. The stopper can be also designed to create a certain engagement in order to increase the force required to tilt the lid portion 40*a* back from the maximum open position and/or to create a "clicking sensation" to signal to the user that the maximum open position is reached.

The hinge mechanism 41 can be provided as operative element for only one of the reservoir 20 and the membrane support 10 but can be without function for the other as long as the required sealing engagement of the lid portion 40*a* is implemented.

The filtration assembly 1 may comprise a media cassette 50 as a further element which is configured to be filled with or which is already provided with a nutrient medium 51 selected for promoting the growth of the microorganism of interest. The media cassette 50 is removably and air-tightly, preferably by a frictional and/or form-locking engagement, for example a bayonet fit, a threaded engagement, a press fit or a snap-fit, attachable to the membrane support 10 at the bottom side, i.e. at the side where the drain member is to be attached but with the drain member 30 being not attached any longer, such that the membrane 11 can get in contact with the nutrient medium 51. The connection between the media cassette 50 and the membrane support 10 should be designed such that it provides sufficient resistance to disengagement of the media cassette 50 from the membrane support 10 so as to enable the combined unit to be handled and transported without the media cassette 50 falling off from the membrane support 10, while still permitting the media cassette 50 to be readily detached from the membrane support 10 if desired in the process.

Figure 10:
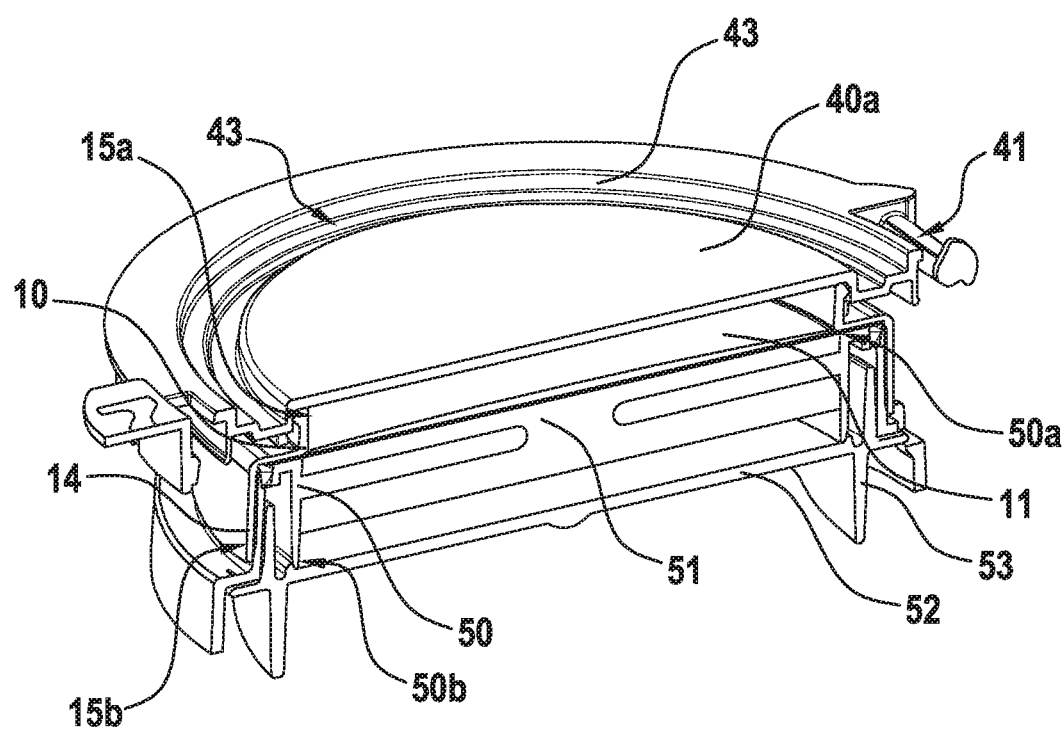
FIG. 10 is a perspective view showing the membrane support of the filtration assembly having the lid device attached to one axial side and a media cassette attached to the other axial side of the membrane support.

The media cassette 50 may be a container with an integrally closed bottom similar to a petri dish and defining a volume for receiving the nutrient medium 51. The media cassette 50 thus has a single opening 50*a* at the top. The opening 50*a* at the top is initially closed after manufacturing by a protective cover (not shown) to prevent any contamination of the nutrient medium 51 or of the pre-sterilized state during transport. Optionally, as shown in FIG. 10, the media cassette 50 has a second opening 50*b* at the bottom of the media cassette 50 which is removably covered with a bottom closure 52. The bottom closure 52 is configured to be placed on the top side of the lid device 40 and is restricted with respect to a lateral movement by one or more protrusion(s) 53 configured to be inserted into a corresponding recess 43 on the top side of the lid device 40 so that the media cassette 50 can be stably piled on top of another media cassette 50 having the membrane support 10 and the lid device 40 attached as described below. When the membrane support 10 is to be attached to the media cassette 50 in order to prepare for the incubation, the protective cover is removed and discarded.

The nutrient medium 51, preferably an agar nutrient, is preferably disposed inside the media cassette 50 so as to have an upward bulge or bump in a central portion and so as to preferentially come in contact with a central portion of the membrane 11 when the media cassette 50 is attached to the membrane support 10. Thus, when the membrane support 10 with the membrane 11 is attached to the media cassette 50 from the top in a vertical downward movement, the nutrient medium 51 is first brought in contact with the central portion of the membrane 11 and is, upon further vertical movement until the attachment is completed, pushed radially outward towards the circumference of the media cassette 50. This progressing contact from the central portion to the periphery ensures a good contact between the membrane 11 and the nutrient medium 51 and avoids the trapping of air bubbles between the nutrient medium 51 and the membrane 11. The central upward bulge or bump of the nutrient medium 51 can be achieved by a slight curvature of the supporting surface for the medium, for example.

This effect of the progressing radial contact between membrane 11 and nutrient medium 51 is enhanced where the membrane 11 has a central downward curvature following the filtration step using the drain member 30 provided with the concave collecting surface 30*a* as described above. Further, in case the filtration process is executed in a clean room having a slight overpressure as compared to the outside of the clean room, the sample volume 12 of the reservoir 20 of the filtration assembly 1 will have the same overpressure at the end of the filtration step. If the lid device 40 is moved to the position where it (fluid-tightly) seals the top opening of the reservoir 20, before the filtration assembly is removed from the clean room, the overpressure inside the reservoir 20 will be conserved for a certain time until the filtration assembly is detached from the drain member and will enhance the outward bulging of the membrane 11.

When the reservoir 20 has been detached from the membrane support 10 in preparation of the incubation step, the lid device 40 can be detached from the reservoir 20 and re-attached to the top opening of the membrane support 10. The lid device 40 after attaching due to the hinge may be selectively brought into the position where it closes the opening but allows venting into the opening, or into the position where it fluid-tightly seals the opening of the membrane support 10. Thus, a desired incubation condition may be set, i.e. anaerobic or aerobic. Even if the venting position of the lid device 40 is set, an inadvertent full closure to the seal position is prevented and the incubation units can be stacked on one another.

The casing-related or support-related constituent elements of the filtration assembly 1 including the membrane support 10, the reservoir 20, the lid device 40, the drain member 30 and the media cassette 50 are preferably made of a thermoplastic resin, preferably of polypropylene, but can be made from other suitable materials depending on the particular design (one way use or multiple use). It is also possible to make certain elements or parts of elements from different materials.

At least some but preferably all constituent elements of the filtration assembly are pre-sterilized during manufacturing and sealed for subsequent use. Moreover, the membrane support 10, the reservoir 20, the drain member 30 and the lid device 40 may be preassembled to form a unit that is ready to use.

There are various nutrient solutions that may be provided in the media cassette 50 and there are various filtration membranes to be used depending on the microorganisms of interest to be filtered and cultivated.

In order to clearly identify and distinguish the respective nutrient solutions and filtration media in order to avoid errors in selecting and matching the solutions and filtration media, the membrane support 10 and the media cassette 50 may be provided with a colour coding to facilitate the identification.

Hereinafter, a method of using the filtration assembly 1 according to the above described embodiment of the present invention will be described. Before the filtration is started the filtration assembly 1 is prepared which has the lower opening of the reservoir 20 attached to the top axial side of the membrane support 10, the lid device 40 attached to the top opening of the reservoir 20, and the drain member 30 attached to the lower axial side of the membrane support 10. The filtration assembly 1 can be substantially pre-assembled as a unit in a pre-sterilized packing or can be assembled at the workplace from the individual elements. After unpacking the filtration assembly 1 is transferred to a head of the external suction or vacuum device (i.e. a vacuum pump or vacuum bar potentially located inside the clean bench) as a unit in one single step and the unit is mounted to the head via the drain member 30 that is held in the membrane support 10. In this connection the pump head is radially expanded in order to sealingly engage the inner peripheral surface of the skirt 35 of the drain member 30 and to establish a fluid connection with the discharge port 33 of the drain member 30.

In the next step an amount of fluid to be filtered is filled into the sample volume 12 of the reservoir 20, the lid portion 40a is brought into the position so as to allow a defined venting, and then the suction device is operated to apply the reduced pressure to the downstream side of the membrane 11 via the discharge port 33 until the desired amount of fluid has passed through the membrane 11. The operation of the suction device is stopped and the filtration assembly including the membrane support 10 and the reservoir 20 is removed as a unit from the head of suction device leaving the drain member 30 attached to the head, thereby removing the membrane support 10 from the drain member 30. Subsequently the membrane support 10 of the filtration assembly is attached to the media cassette 50 such that the membrane 11 comes in contact with the nutrient medium 51, the reservoir 20 is removed from the membrane support 10, and the lid device 40 is removed from the reservoir 20 and re-attached to the top opening of the membrane support 10 to close or even seal the media cassette 50 depending on the position of the lid device 40 allowing the defined venting or creating a complete fluid-tight seal of the top opening of the membrane support.

Figure 6B:
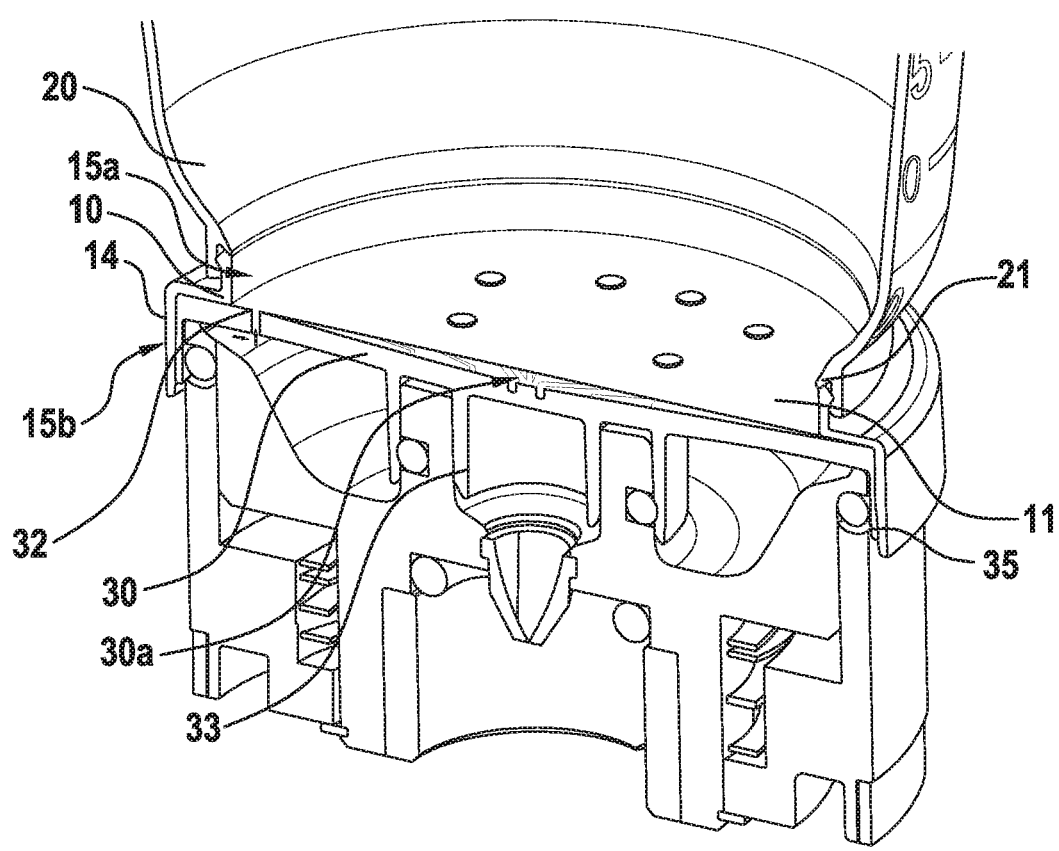
FIG. 6B is an enlarged perspective sectional view showing a part of the filtration assembly according to the embodiment when mounted on the suction device during a membrane drying step.
Figure 7:
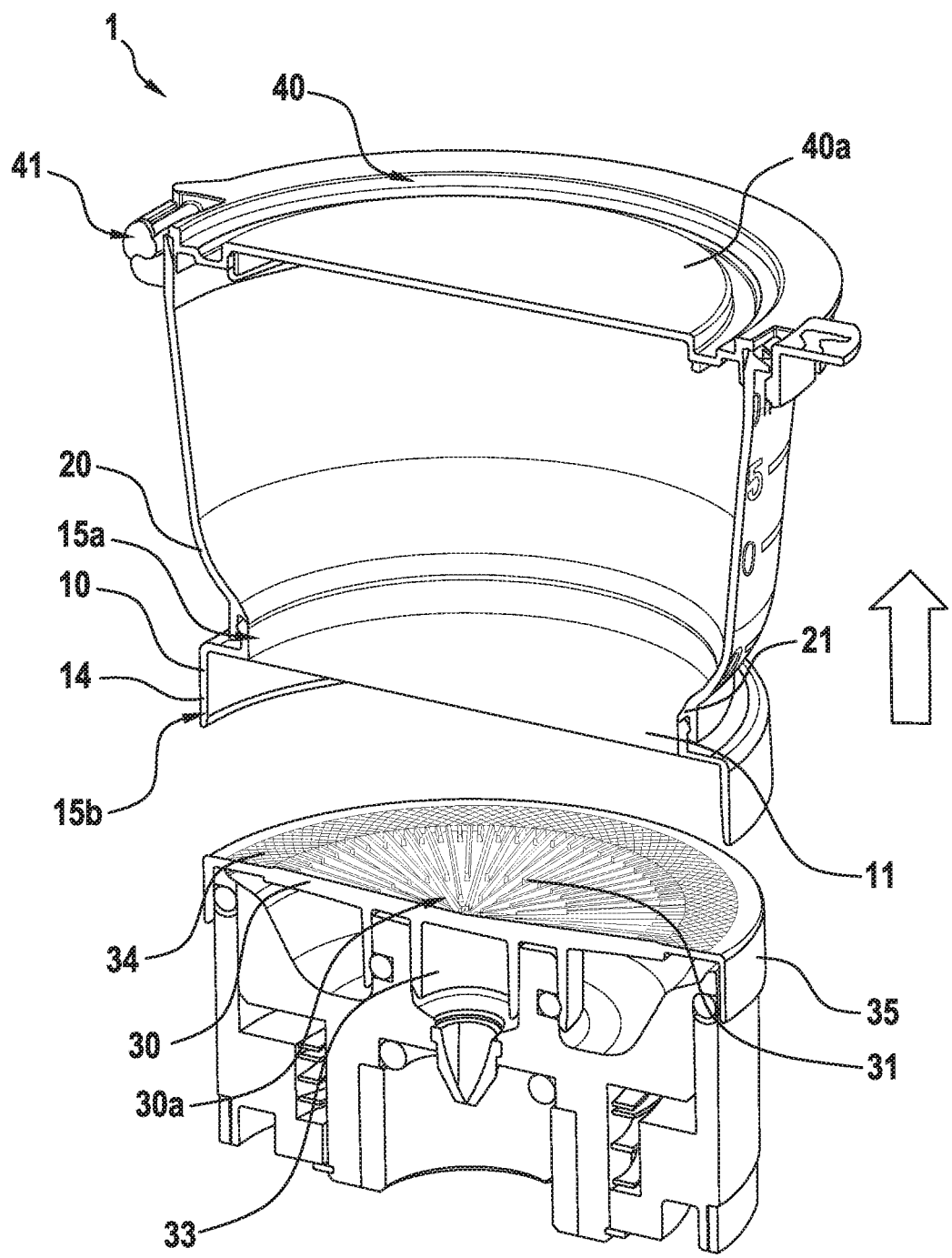
FIG. 7 is a perspective sectional view of the filtration assembly according to the embodiment when the membrane holder with the reservoir is pulled from the filtration head leaving the drain member held by the head.

The filtration method may further comprise, during the step of operating the suction device, in order to dry the membrane 11 and purge the space between the lower side of the membrane 11 and the collecting surface 30a of the drain member 30 from residual fluid, moving of the lid device 40 into the position where it seals the top opening of the reservoir 20, and allowing ambient air to pass into the space between the membrane 11 and the collecting surface 30a of the drain member 30 via the venting opening(s) 32, the circular air groove 34 and the radial flow channel(s) 31 while applying the suction force through the discharge port 33 as described above in connection with FIG. 6.

REFERENCE SIGNS 1 filtration assembly
10 ring-like membrane support
11 filtration membrane
12 sample volume
13 drain channel space
14 skirt
15a,15b openings of membrane support
20 reservoir
20a,20b openings of reservoir
21 lip portion
22 snap-fit connection
23 engagement rim or protrusion of reservoir
24 engagement rim or protrusion of membrane support
30 drain member
30a collecting surface or collecting zone
31 radial flow channels
32 venting opening
33 discharge port
34 circular air groove
35 skirt
36 peripheral zone
40 lid device
41 hinge
40a lid portion
43 recess
50 media cassette
50a top opening
50b bottom opening
51 nutrient medium
52 bottom closure
53 protrusion

The invention claimed is:

1. A filtration assembly (1) for microbiological testing, comprising:
a ring-like membrane support (10) holding a filtration membrane (11);
a cylindrical reservoir (20) of which opposite first and second axial ends have openings and a first axial opening is removably and fluid-tightly attachable to the membrane support (10) to define a sample volume adjacent to the filtration membrane (11) on a first axial side of the membrane support (10); and
a drain member (30) removably and fluid tightly attachable to the membrane support (10) to define a drain channel space adjacent to the filtration membrane (11) on a second axial side of the membrane support (10), said drain member (30) having a collecting surface (30a) facing the filtration membrane (11) for collecting fluid having passed through the filtration membrane (11) formed on the membrane support (10), and said drain member (30) further comprises a venting opening (32) penetrating the collecting surface (30a) of the drain member (30) from one side of the collecting surface (30a) to another side of the collecting surface (30a) to allow ambient air to be supplied to the collecting surface (30a), wherein said venting opening (32) is disposed on a radial outer periphery of the collecting surface (30a).

2. The filtration assembly (1) according to claim 1, further comprising:
a lid device (40) which is removably and fluid tightly attachable to the second axial opening of the reservoir (20) to close the second axial opening, and is removably and fluid tightly attachable to the membrane support (10),
wherein the lid device (40) has a hinge (41) for supporting a lid portion (40a) so as to allow selective opening of the lid device (40) with a predefined movement,
wherein the hinge (41) is either included in the lid device (40) or a first part of the hinge (41) is provided on the reservoir (20) and/or on the membrane support (10) and a second part of the hinge (41) is provided on the lid device (40).

3. The filtration assembly (1) according to claim 2, wherein the lid device (40) is formed so as to provide at least three defined positions of the lid portion (40a) including a first position where the lid portion (40a) seals the second axial opening, a second position where the second axial opening is accessible and the lid portion (40a) is preferably restricted by a mechanical stopper, and a third position where the lid portion closes the opening but allows a defined venting into the second axial opening.

4. The filtration assembly (1) according to claim 1, wherein the drain member (30) is removably attachable to the membrane support (10) by means for frictional and/or form-locking engagement.

5. The filtration assembly (1) according to claim 4, wherein the drain member (30) is received in a skirt portion surrounding the opposite axial side of the membrane support (10).

6. The filtration assembly (1) according to claim 1, wherein
the collecting surface is concave with an apex spaced apart from the filtration membrane (11) when the drain member (30) is attached to the membrane support (10), and
said drain member (30) further comprises one or more radial flow channel(s) (31) formed on the collecting surface (30a), and
a discharge port (33) for discharging the fluid collected on the collecting surface (30a) to a side opposite to the collecting surface.

7. The filtration assembly (1) according to claim 6, wherein the collecting surface (30a) of the drain member (30) has a smaller radius than the filtration membrane (11) held in the membrane support (10) and is spaced from an outer circumference of the filtration membrane (11).

8. The filtration assembly (1) according to claim 1, wherein the reservoir (20) is removably attachable to the membrane support (10) by means for frictional and/or form-locking engagement.

9. The filtration assembly (1) according to claim 1, wherein a cross sectional area defining the sample volume (12) of the reservoir (20), perpendicular to an axial direction of the reservoir (20), gradually increases at least in a portion adjacent to the first axial opening of the reservoir (20) to be attached to the membrane support (10), towards a second axial opening of the reservoir (20).

10. The filtration assembly (1) according to claim 9, wherein the reservoir (20) has a lip portion (20a) with an acute tip end protruding radially inward at the opening of the reservoir (20) to be attached to the membrane support (10).

11. The filtration assembly (1) according to claim 3, further comprising:
a media cassette (50) configured to hold a nutrient medium (51), wherein the media cassette (50) is removably and air-tightly attachable to the membrane support (10) at the second axial side of the membrane support (10) when the drain member (30) is not attached to the second axial side of the membrane support (1), such that the filtration membrane (11) is in contact with the nutrient medium (51).

12. The filtration assembly (1) according to claim 11, wherein a nutrient medium (51) is disposed inside the media cassette (50) so as to have an upward bulge in a central portion.

13. A method of filtrating a fluid using the filtration assembly (1) according to claim 11, comprising the steps of:
preparing the filtration assembly which has the first axial opening of the reservoir (20) attached to the first axial side of the membrane support (10), the lid device (40) attached to the second axial opening of the reservoir (20), and the drain member (30) attached to the second axial side of the membrane support (10),
mounting the second axial side of the membrane support (10) with the drain member (30) on a suction device,
filling an amount of fluid to be filtrated into the sample volume of the reservoir (20),
moving the lid portion into the third position,
operating the suction device until a desired amount of the fluid has passed through the filtration membrane (11),
removing the membrane support (10) from the drain member (30),
attaching the membrane support (10) to the media cassette (50) such that the filtration membrane (11) comes in contact with the nutrient medium (51),
removing the reservoir (20) from the membrane support (10) and removing the lid device (40) from the reservoir (20),
re-attaching the lid device (40) to a top opening on the first axial side of the membrane support (10), and
moving the lid portion (40a) of the lid device (40) into a fourth position so as to allow a defined venting or as to seal the top opening of the membrane support (10).

14. The method of filtrating a fluid according to claim 13, further comprising the following steps during the step of operating the suction device:
moving the lid device (40) into the position where it sealing the second axial opening of the reservoir (20), and
allowing ambient air to pass into a space between the filtration membrane (11) and a collecting surface (30a) of the drain member (30) to dry the filtration membrane (11).

15. The filtration assembly (1) according to claim 4, wherein the drain member (30) is removably attachable to the membrane support (10) by means for snap-fit engagement.

16. The filtration assembly (1) according to claim 6, wherein the venting opening (32) allows the ambient air to be supplied to the collecting surface (30a) via a circular air groove (34) formed on the surface of the drain member (30) facing the filtration membrane (11) and surrounding the collecting surface and in communication with the radial flow channel(s) (31) thereof.

17. The filtration assembly (1) according to claim 8, wherein the reservoir (20) is removably attachable to the membrane support (10) by means for snap-fit engagement.

18. The filtration assembly (1) according to claim 11, wherein the media cassette (50) is removably and air-tightly attachable to the membrane support (10) via a frictional and/or form-locking engagement.

19. The filtration assembly (1) according to claim 12, wherein the nutrient medium (51) is an agar nutrient and is disposed inside the media cassette (50) so as to come in contact with a central portion of the filtration membrane (11) when the media cassette is attached to the membrane support (10).

* * * * *